United States Patent [19]

Bressan

[11] 4,087,743

[45] May 2, 1978

[54] FOG-WATER CONDUCTIVITY MEASURING DEVICE

[75] Inventor: David J. Bressan, Forestville, Md.

[73] Assignee: The United States of America as represented by the Secretary of the Navy, Washington, D.C.

[21] Appl. No.: 707,408

[22] Filed: Jul. 21, 1976

[51] Int. Cl.² .............................................. G01N 27/42
[52] U.S. Cl. ..................................... 324/30 R; 73/28; 204/195 P; 324/65 P
[58] Field of Search ................. 324/65 P, 30 R, 30 A, 324/36; 73/28, 29; 340/237 P; 204/195 W, 195 P

[56] References Cited

U.S. PATENT DOCUMENTS

| 3,105,214 | 9/1963 | Blythe et al. | 324/65 P |
| 3,139,085 | 6/1964 | Custance et al. | 324/65 P |
| 3,430,483 | 3/1969 | Clawson et al. | 73/29 |
| 3,444,092 | 5/1969 | Truhan | 73/29 |
| 3,473,118 | 10/1969 | Tassicker et al. | 73/28 |
| 3,847,777 | 11/1974 | Haddad | 204/195 P |

Primary Examiner—Rudolph V. Rolinec
Assistant Examiner—Michael J. Tokar
Attorney, Agent, or Firm—R. S. Sciascia; Philip Schneider; Melvin L. Crane

[57] ABSTRACT

A system for automatically sampling fog-water at a known rate, for determining the electrical conductivity, and for retaining fog-water samples for additional related study. The conductivity of the collected water is used to estimate total salt content of the fog and/or air, which determines the availability of salts to act as the condensation nuclei for fog and haze.

13 Claims, 4 Drawing Figures

FOG-WATER CONDUCTIVITY MEASURING DEVICE

BACKGROUND OF THE INVENTION

This invention relates to marine fog studies and more particularly to a system for automatically collecting fog-water and estimating the salt content thereof in real time.

A prior art method made use of a single-mesh nylon screen panel or fog kite of 1 square meter size for fog collection. In use of that device, air would spill around the panel making quantitative estimates from that device difficult. It has been determined that for a thirty knot wind, 40% of the air would be lost by spilling around the panel, and the percentage varies with windspeed, compounding the difficulties. This method requires constant attendance, and does not give any kind of real-time read out.

SUMMARY OF THE INVENTION

This invention makes use of a pipe through which foggy air is aspirated at a specific known rate. Liquid water is collected by spaced nylon mesh and fed by gravity into a conductivity cell which yields an estimation of the salt content. The conductivity cell automatically empties through a siphon. This system permits one to collect a specific amount (volume) of fog-water, have the collected volume automatically measured for conductivity and have the cell automatically emptied into a collection bottle to retain a time-wise integrated sample.

DETAILED DESCRIPTION

The fog conductivity-measuring device of the present invention comprises three sections. The foggy air is sampled at a chosen rate of about 148 cubic feet per minute and the liquid water is collected automatically by a specially designed fog-water collector means. The liquid water so collected is fed by gravity into a collector container-siphon system which is provided with a conductivity cell that measures the conductivity of the water as it is collected. When the collected water reaches a particular height in the collector, the water is automatically siphoned into a clean bottle where it is stored for later analysis. An electrical circuit is provided to operate and control the various elements.

Figure 1:
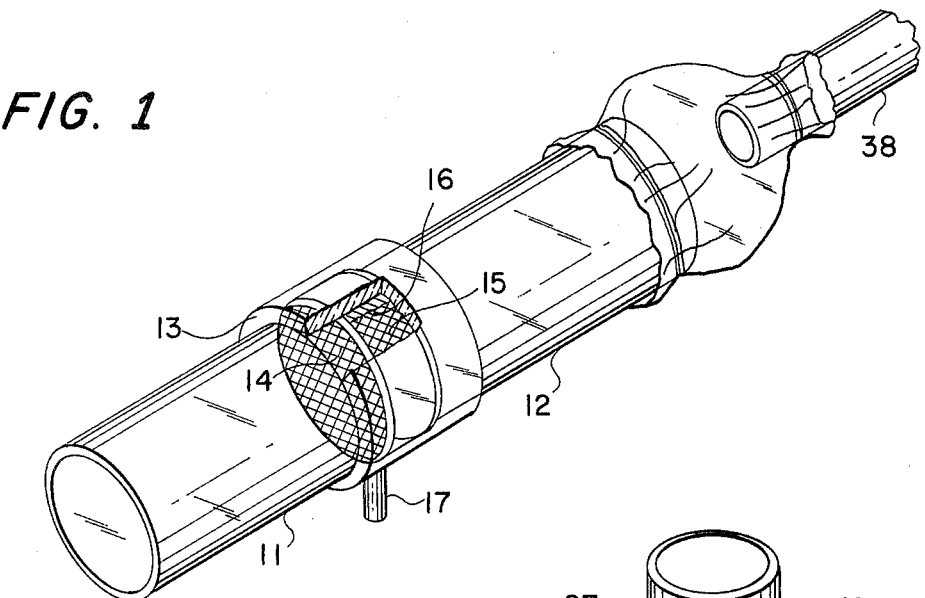
FIG. 1 illustrates a foggy air and liquid water collector in combination with a gravity-fed, water-collecting conductivity cell from which water is automatically siphoned.
Figure 2:
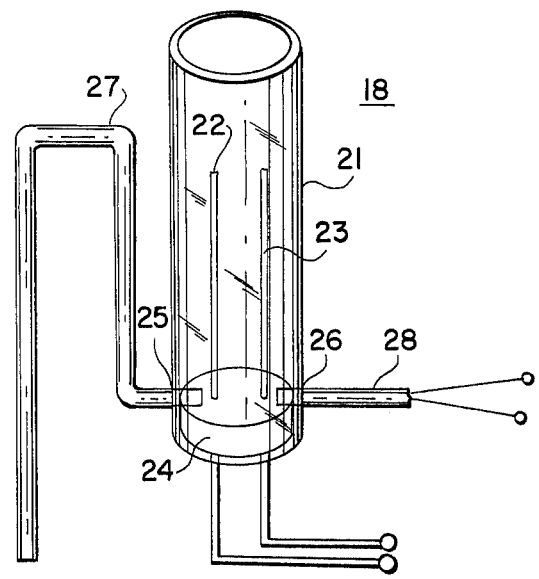
FIG. 2 illustrates a conductivity-cell water-collector siphon.

The fog collection device is made with an inlet plastic pipe 11 and an outlet plastic pipe 12 each of which have an outside diameter of 6 inches with an inside diameter of 5½ inches. Adjacent ends of the inlet pipe and outlet pipe are coupled together with an acrylic tube coupling 13 so that the coupled ends are spaced from each other. In the spacing between the ends of the pipe, there is assembled on the inside of the coupling first and second nylon mesh 14 and 15 separated from each other by a plastic spacer-ring 16. The nylon mesh may be NITEX 706 formed with 27 strands per inch with a strand diameter of 0.011 inches. The coupling 13 is provided with a drain pipe 17 on the bottom through which collected water passes to a water collector 18, FIG. 2.

The water collector 18 is made with an automatic siphon 27 which is operative to siphon water from the container as the container fills to a certain height. The water so siphoned from the container is transferred into bottles and these samples are used for further analysis in a laboratory. The water collector 18 has associated therewith a conductivity-measuring cell such as a Yellow Springs Instrument #3418 conductivity cell having a cell constant of 0.10 cm/cm$^2$ and manufactured by Yellow Springs Instrument Company. The conductivity cell so mentioned is made with an open-ended tube 21 within which spaced electrodes 22, 23 are inserted through an insulator 24 and held in place thereby. The insulator closes off the end of the tube 21 in which it is inserted. The tube 21 is provided with two holes 25, 26 near the insulator. These holes are used to connect the siphon 27 to the tube and to insert the thermistor 28 into the cell. The conductivity cell is turned with the open end up so that the closed end is down; thus the tube becomes the water collector. The siphon is made from a small tube bent into a U-shape with the "U" or hump up so that the siphon extends along the length of the tube. Thus, as the collector fills, water also enters the siphon tube. Once the water level fills the siphon tube up to the hump, water will spill over the hump to produce the siphon effect. Thus, the water is automatically dumped and collected in a larger storage bottle. The physical configuration of the water collector-siphon conductivity cell is such that the collector will fill to a volume of about 2 milliliters before the water is automatically dumped by the action of the siphon. The conductivity cell is temperature-compensated with a 33A57 thermistor 28 (2500 ohms at 25° C) and a 250 ohm variable resistor 67 in the circuit. The conductivity values determined by conductivity cell are read out with a 0–500 μA meter 74, and a strip chart recorder 80 records the output. Prior to use, the instrument is calibrated by use of known solutions of NaCl and diluted seawater and the milliampere read-out is converted to milligrams NaCl per liter by use of a graph. Graphs of different-value solutions may be made for comparison with the values measured by the conductivity cell.

Figure 3:
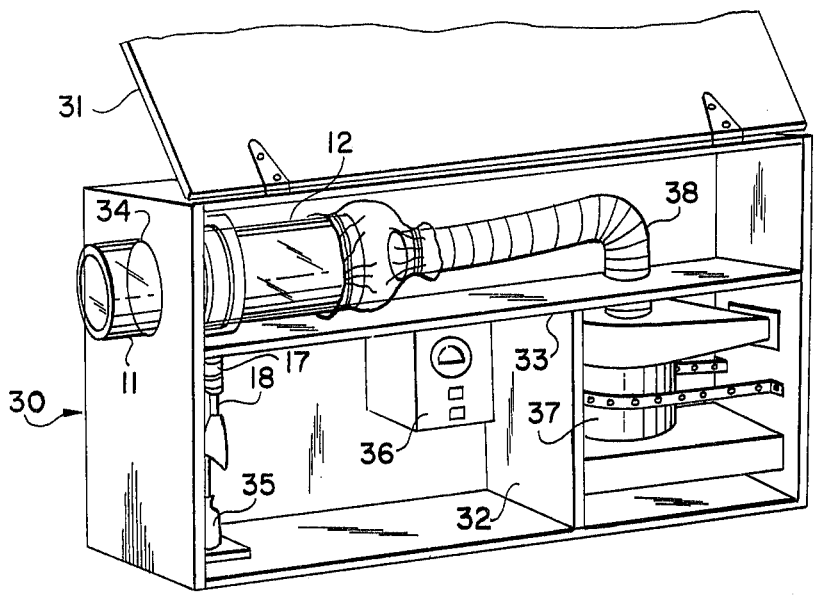
FIG. 3 illustrates a housing within which the fog collector and measuring system is housed.
Figure 4:
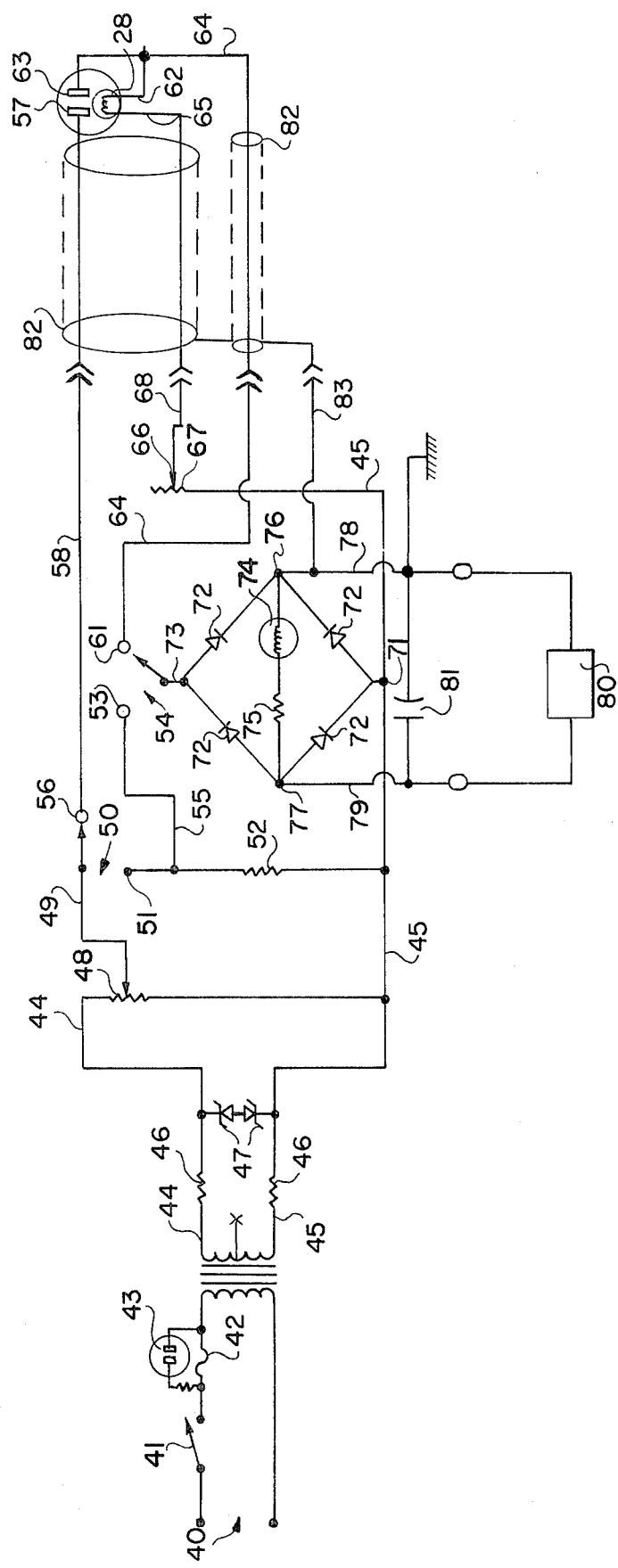
FIG. 4 is a schematic of the electrical circuitry for the system.

FIG. 3 illustrates a housing 30 within which the various elements are assembled in order to secure the elements in place relative to each other. The housing is made such that it opens on one side with the side closure 31 hinged at the top. As shown, the side closure is open so the inside of the housing is exposed. The lower portion of the housing is provided with a removable partition 32 and the housing is provided with a removable shelf 33 which extends across the middle above the partition 32. The left end as shown is provided with a 6 inch opening 34 through which the inlet end 11 of the fog collector extends to the outside. The fog collector is supported on the shelf with its linear axis toward the opposite end of the housing. The drain tube 17 extends through an opening in the shelf so that the drain pipe extends into the top of the water collector-siphon 18 which is secured in place to the housing end below the shelf. The plastic bottle 35 for collecting the water from the siphon is supported by the bottom of the housing so that the tube from the siphon extends into the upper end of the plastic bottle. The plastic bottle used will hold 60 milliliters of water and must be changed by hand. Of course, the collector-siphon contains the conductivity cell for measuring the conductivity of the water, and the thermistor for monitoring the water temperature and automatically providing necessary electronic compensation to obtain accurate readings from the output devices. The box 36 contains the conductivity bridge, milliammeter and the controls therefor. Suitable electrical lines connect with the bridge, for feeding a current to the bridge and for connecting the bridge with the conductivity cell, as shown in FIG. 4. An air blower 37 located in the lower area of the housing near the right end is connected directly with the output end of the fog collector by use of a plastic bonnet and flexible hose 38 so that the blower draws the fog through the fog collector at the flow rate of 148 CFM. The air from the blower is exhausted through a three-inch opening in the right end of the housing.

The electrical circuitry is shown in a schematic drawing in FIG. 4. A 110 volt AC, 60 cycle source 40 is used for a power supply. One power supply line includes a main switch 41, a fuse 42, and a blown fuse indicator 43. The input lines from the source are connected to a filament transformer which reduces the voltage from 110 volts to 6.8 volts. Each line 44, 45 from the transformer includes a 50 ohm resistor 46 with a pair of 1N3997A 5.6 volt zener diodes 47 connected back-to-back across the lines 44, 45 in parallel with a 500 ohm variable resistor 48. The take-off line 49 from the variable resistor 48 is connected with a single-pole double-throw switch 50. One pole 51 of the switch 50 connects with one side of a 2700 ohm resistor 52 and to one pole 53 of a second double-pole single-throw switch 54 through line 55. The pole 56 of switch 50 connects with one electrode 57 of the conductivity cell by use of line 58. The other pole 61 of the switch 54 connects with one side 62 of the thermistor and to the other electrode 63 of the conductivity cell by line 64. The opposite side 65 of the thermistor connects with a take-off contact 66 of a 250 ohm variable resistor 67 through line 68. The opposite side of resistor 52 connects with line 45 which is connected to the electrical bridge at 71 and to the variable resistor 67.

The electrical bridge includes a 1N914 diode 72 in each of its legs with the bridge connected to the contact of a movable arm of switch 54 and 73. The bridge includes a 0–500 $\mu$A., DC Ammeter 74 in series with a 2000 ohm resistor 75 connected between points 76 and 77. Output lines 78 and 79 are connected respectively to points 76 and 77 and to strip chart recorder 80 and/or to a computer for recording the output information. A 50 mfd, 25 v, DC capacitor 81 is connected between output lines 78 and 79 and output line 78 is connected to ground. Each of the conductive lines connected to the conductivity cell and the thermistor are enclosed in a shielded cable 82 which is connected to ground through line 83.

The double-pole single-throw switches 50 and 54 permit an operator to set the switches in one position so that the thermistor and conductivity cells are not in the circuit. In the set position, the ammeter may be set to its full-scale reading by adjustment of the variable resistor 48. Once the ammeter has been calibrated, the switches 50 and 54 may be moved to the run position. In this position the thermistor and the conductivity cell are in the circuit and the system is ready for operation.

In operation, the switches 50 and 54 are positioned in the set positions and the main switch is closed. The ammeter 74 is calibrated and the system is ready to go.

The main switch is opened to check for a zero reading on the output devices, and the switches 50 and 54 are positioned in the run position. The main switch 41 is closed and the blower pulls the foggy water into the fog collector. As the foggy air passes through the nylon mesh, the fog water is stripped from the air and the air is exhausted through the output of the blower. The water collected by the nylon mesh flows to the bottom of the coupler, out through the drain pipe and into the collector-siphon conductivity cell. The conductivity cell measures the conductivity of the water, while the thermistor provides the necessary compensation for differences in temperature. The output measurement of the conductivity cell is recorded on the stripchart. By observation of the stripchart, the conductivity of the cell can be seen to rise as the cell fills. The conductivity value levels off as the cell continues to fill to its full volume, then drops to less than 5 percent of the peak reading as the siphon drains the cell. The siphoned water is collected by large plastic bottles for future analysis. The collector-siphon fills until the water rises slightly above the turn or hump in the siphon tube. As the water flows over the turn, the siphon will drain the collector-siphon-conductivity cell. Once drained, the collector-siphon will begin to fill again and continue filling with subsequent draining as long as there is fog and the system is operated. A record of the conductivity measurement is made by the strip recorder or computer or any other suitable recorder. The amount of NaCl or sea salt is then determined by comparing the recorded values with those shown on the graphs which were previously made from solutions of known concentrations.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A fog-conductivity measuring system which comprises:
    foggy air collector means;
    means interconnected with said foggy air collector means for introducing a sample of foggy air into said foggy air collector means;
    means within said foggy air collector means for separating fog water from the foggy air;
    means for collecting said fog water;
    means within said fog water collecting means for measuring the conductivity of said collected fog water during collection; and
    means for recording the measured conductivity of said collected fog water.

2. A fog-conductivity measuring system as claimed in claim 1 which includes:
    siphon means for automatically dumping said collected fog water into a separate storage container.

3. A fog-conductivity measuring system as claimed in claim 1 wherein;
    said foggy air is introduced at a rate of about 148 cfm.

4. A fog-conductivity measuring system as claimed in claim 3 wherein;
    said means for measuring the conductivity of said collected fog water is a conductivity cell.

5. A fog-conductivity measuring system which comprises:
    foggy air collector means;

means interconnected with said foggy air collector means for introducing a sample of foggy air into said foggy air collector means;

a pair of spaced nylon meshes in tandem within said foggy air collector means for separating fog water from the foggy air;

means for collecting said fog water;

means within said fog water collecting means for measuring the conductivity of said collected fog water during collection; and means for recording the measured conductivity of said collected fog water.

6. A fog-conductivity measuring system as claimed in claim 5 which includes:

siphon means for automatically dumping said collected fog water into a separate storage container.

7. A fog-conductivity measuring system as claimed in claim 5 wherein:

said fog water collector includes a siphon means for automatically dumping said collected fog water into a sepaerate storage container.

8. A fog-conductivity measuring system as claimed in claim 7 wherein:

said means for measuring the conductivity of said collected fog water is a conductivity cell.

9. A fog-conductivity measuring system as claimed in claim 5 wherein;

each of said nylon meshes have strands with a diameter of 0.011 inches with 27 strands per inch.

10. A fog-conductivity measuring system as claimed in claim 5 which includes:

aspirator means for introducing foggy air into said foggy air collector means.

11. A fog-conductivity measuring system as claimed in claim 10 wherein:

said foggy air is introduced into said foggy air collector means at a rate of about 148 cfm.

12. A fog-conductivity measuring system as claimed in claim 5 wherein:

said means for measuring the conductivity of said collected fog water is a conductivity cell.

13. A fog-conductivity measuring system as claimed in claim 3 in which:

said foggy air is introduced by an aspirator.

* * * * *